(12) United States Patent
Castillo-Welter et al.

(10) Patent No.: US 8,431,696 B2
(45) Date of Patent: *Apr. 30, 2013

(54) METHOD FOR CONTINUOUSLY PRODUCING MELAMINE

(75) Inventors: Frank Castillo-Welter, Friedrichsdorf (DE); Christoph Steden, Oberursel (DE); Dominic Walter, Darmstadt (DE); Georg Ehring, Frankfurt (DE); Martin Müller-Hasky, Heusenstamm (DE)

(73) Assignee: Lurgi GmbH, Frankfurt am Main (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/394,917

(22) PCT Filed: Sep. 24, 2010

(86) PCT No.: PCT/DE2010/001135
§ 371 (c)(1),
(2), (4) Date: Apr. 19, 2012

(87) PCT Pub. No.: WO2011/057596
PCT Pub. Date: May 19, 2011

(65) Prior Publication Data
US 2012/0232269 A1    Sep. 13, 2012

(30) Foreign Application Priority Data
Nov. 10, 2009    (DE) .................. 10 2009 052 420

(51) Int. Cl.
*C07D 251/60*    (2006.01)
*C07D 251/62*    (2006.01)

(52) U.S. Cl.
USPC .......................................... 544/203; 544/201

(58) Field of Classification Search .................. 544/201, 544/203
See application file for complete search history.

(56) References Cited

U.S. PATENT DOCUMENTS

| | | | |
|---|---|---|---|
| 3,895,007 A * | 7/1975 | Schwarzmann et al. ...... | 544/201 |
| 4,348,520 A * | 9/1982 | Bruls et al. .................... | 544/201 |
| 7,977,479 B2 * | 7/2011 | Muller-Hasky et al. ...... | 544/201 |
| 8,058,428 B2 * | 11/2011 | Muller-Hasky et al. ...... | 544/203 |

FOREIGN PATENT DOCUMENTS

| | | |
|---|---|---|
| CN | 1188761 A | 7/1998 |
| WO | 2006/119815 A1 | 11/2006 |
| WO | 2008098732 A1 | 8/2008 |

OTHER PUBLICATIONS

International Search Report dated Apr. 13, 2011, mailed Apr. 19, 2011.

* cited by examiner

*Primary Examiner* — Venkataraman Balasubramanian
(74) *Attorney, Agent, or Firm* — Norris McLaughlin & Marcus PA

(57) ABSTRACT

A process for the continuous production of melamine from urea by means of a fluidized-bed reactor, wherein process gas guided in the process circuit is used as fluidizing gas and wherein the temperature of the process gas at the inlet of the conveying means for the fluidizing gas is adjusted by adjusting the mixing ratio of a process gas stream guided over a scrubber and of a process gas stream guided past the scrubber.

4 Claims, 1 Drawing Sheet

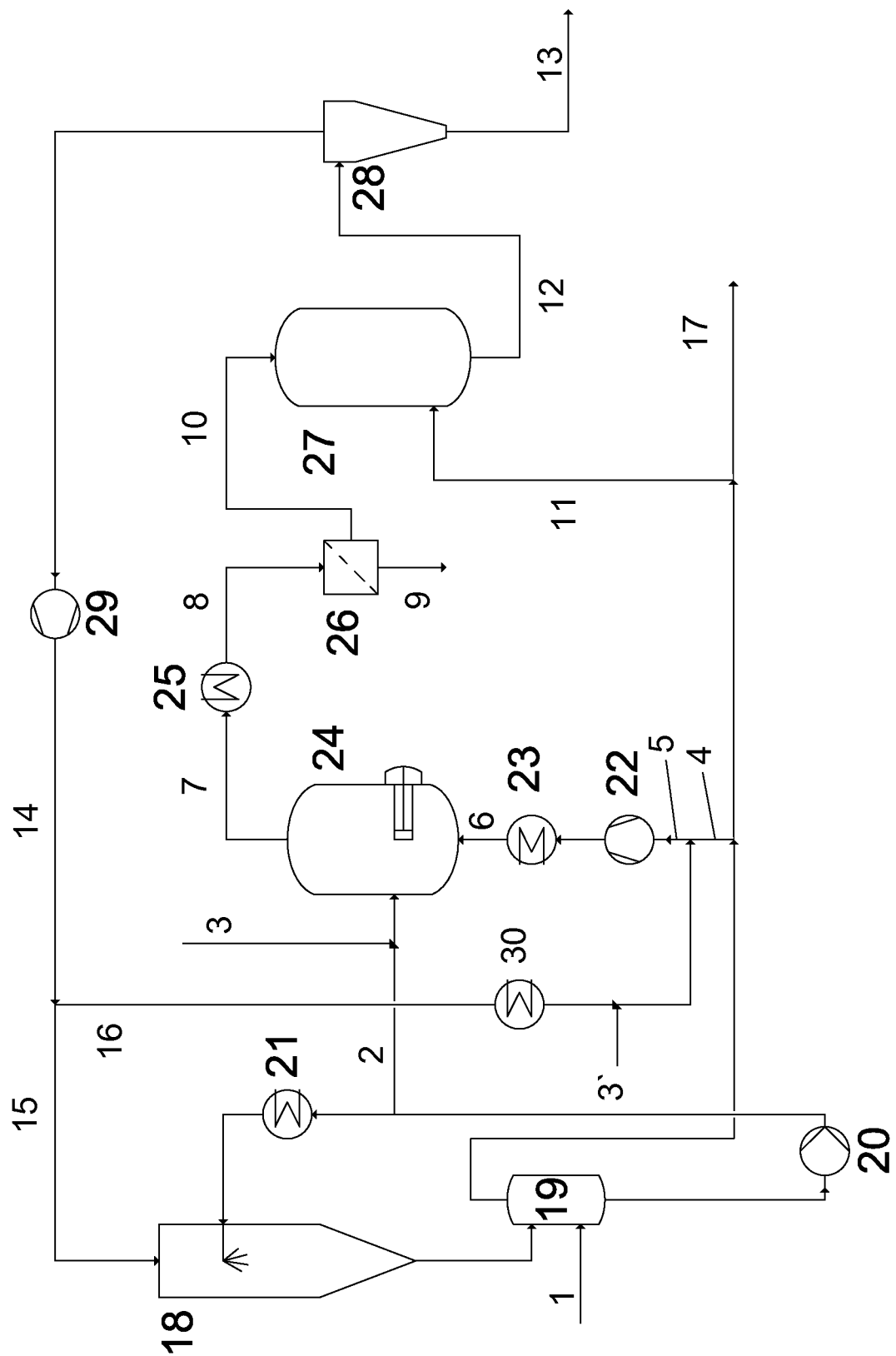

METHOD FOR CONTINUOUSLY PRODUCING MELAMINE

This is a 371 of PCT/DE2010/001135 filed 24 Sep. 2010 (international filing date), claiming priority of German application 10 2009 052 420.7 filed 10 Nov. 2009.

This invention relates to a process for the continuous production of melamine, wherein in a fluidized-bed reactor, in the presence of a catalyst, by supplying heat and by adding ammonia, the liquid urea used as starting material is converted into a process gas, chiefly consisting of melamine, ammonia, carbon dioxide, the intermediate product isocyanic acid and by-products, and wherein this process gas, after the by-products and the melamine have been separated therefrom, is passed into a scrubber in which it is washed with liquid urea and liberated from the isocyanic acid content, wherein the process gas, after leaving the scrubber, in part is used as fluidizing gas in the fluidized-bed reactor, in part is used as cooling gas in the crystallizer, and in part is discharged from the process gas circuit.

BACKGROUND OF THE INVENTION

Processes for the continuous production of melamine from urea are known. An example is the so-called BASF low-pressure process, as it is described in Ullmann's Encyclopedia of Industrial Chemistry, Sixth Edition, Chap. 4.1.1., 1998 Electronic Release.

The process according to the prior art proceeds at high temperatures in the gas phase. The starting material, the urea, is charged into a fluidized-bed reactor in liquid form, is fluidized therein by a $NH_3$—$CO_2$ process gas mixture, evaporated at temperatures of 390 to 410° C., converted into melamine in the presence of an aluminum catalyst via the intermediate product isocyanic acid, wherein as further reaction products ammonia and carbon dioxide and as by-products melem and melam are obtained. After leaving the fluidized-bed reactor, this gas mixture first is cooled to about 340° C. in a gas cooler, in order to crystallize out the by-products melem and melam, which are separated from the gas stream in a subsequently traversed gas filter, together with catalyst particles entrained from the fluidized-bed reactor. Subsequently, the gas is guided into a crystallizer in which it is cooled to 190 to 220° C. for crystallizing out the melamine. The mixture of the residual gaseous constituents, ammonia, carbon dioxide and isocyanic acid and crystallized powdery melamine, is passed from the crystallizer into a separator in which the melamine is separated from the gas and discharged as process product. By means of a blower, the gaseous constituents are passed from the separator into a scrubber in which the gas is washed with liquid urea, wherein the isocyanic acid contained in the gas and other by-products of the reactions taking place in the fluidized-bed reactor are washed out from the gas, move into the liquid urea and hence remain in the process. From the urea circuit of the scrubber a partial stream is branched off and, mixed with ammonia, fed into the fluidized-bed reactor as starting material for the melamine production. The gas mixture of ammonia and carbon dioxide, which in the scrubber is liberated from isocyanic acid residues, in part is used as fluidizing gas in the fluidized-bed reactor and in part is fed into the crystallizer as cooling gas for crystallizing out the melamine.

In the scrubber, the process gas is cooled down to 135 to 143° C., as a low temperature which lies as close as possible above the melting temperature of the urea of 130 to 135° C., promotes a substantial conversion of the isocyanic acid into urea. In addition, a rather low temperature is advantageous for the use as cooling gas in the crystallizer.

It is characteristic for this BASF low-pressure process that the entire amount of process gas, after separating the melamine, is guided over the scrubber operated with liquid urea, wherein the gaseous and solid product and by-product residues move into the urea and, by being fed into the fluidized-bed reactor together with the same, remain in the process circuit and are not discharged from the process with the excess gas and get lost. In the scrubber, the product and by-product residues for the most part are again converted into urea, so that it is avoided that these substances repeatedly pass through the hot fluidized-bed reactor and thereby form chemical compounds which might contaminate the melamine.

A disadvantage of this treatment of the entire process gas in the scrubber consists in that a process gas saturated with urea thereby also is supplied to the conveying means of the fluidized-bed reactor, so that disturbing urea deposits repeatedly are formed at its inlet.

In another process for producing melamine, which is set forth in the Chinese laid-open specification CN 1188761A, Jiang Dazhou et al., this disadvantage, i.e. the tendency to form urea deposits, has been avoided by completely passing the process gas used as fluidizing gas past the urea scrubber. In this process, the process gas, after leaving the urea scrubber, is completely passed through the melamine crystallizer as cooling gas, is heated up thereby and is supplied to the conveying means of the fluidized-bed reactor with the temperature reached thereby.

In this process it is disadvantageous that the temperature of the process gas necessarily corresponds to the gas temperature existing in the crystallizer and cannot, independent thereof, be adjusted to the temperature optimally suited for the condenser or the blower.

In principle, setting an upper limit for the gas temperature is very important for the manufacturing costs and for the operational safety of a condenser or blower. A gas temperature of about 200° C. should not be exceeded, since at higher temperatures the requirements and hence the costs of the conveying means rise to a great extent.

Therefore, it is the object of the present invention to improve the process to the effect that the temperature of the gas at the inlet of the condenser or the blower of the fluidized-bed reactor can be adjusted such that both urea deposits and an excessive thermal stress of the conveying means is avoided.

SUMMARY OF THE INVENTION

This object is solved in that in flow direction before the scrubber a partial stream is branched off from the process gas stream, guided past the scrubber and in flow direction before the fluidized-bed reactor introduced into the process gas stream serving for fluidization and treated in the scrubber. An advantage of this process consists in that by adjusting the mixing ratio of the gas streams a gas temperature can be adjusted, by which urea deposits at the inlet of the conveying means are avoided and which does not expose the conveying means to too high a thermal stress.

A further advantage of this invention as compared to the BASF low-pressure process consists in that the process gas guided past the scrubber is not unnecessarily deprived of heat which would again have to be supplied in the fluidized-bed reactor. The isocyanic acid content of this partial stream is not re-converted into urea in the scrubber, but can directly be converted into melamine in the fluidized-bed reactor. Another advantage of the invention consists in that the urea scrubber can be constructed smaller and hence less expensive, as it is charged with less process gas.

An advantageous aspect of the invention is characterized in that in the conduit of the partial stream guided past the scrubber an indirect heat exchanger is installed for cooling said partial stream. By cooling the same, its amount in the fluidizing gas can be increased relative to the amount of the gas treated in the scrubber, without changing the temperature of the mixture. In this way, a fine adjustment of the mixture can be effected for optimizing the process in terms of energy consumption, product yield and purity and deposits in the apparatuses.

A further advantageous aspect of the process is characterized in that ammonia is fed into the conduit of the partial stream. Such feeding is effected alternatively or in addition to the use of a heat exchanger and serves the same purpose. Feeding ammonia, directly or together with the urea, into the fluidized-bed reactor hence can be reduced.

A further advantageous aspect of the process is characterized in that in flow direction before the conveying means of the fluidizing gas a static mixer is installed in the conduit, in order to achieve a good intermixture of the gas treated in the scrubber and of the gas guided past the scrubber.

Detailed Description

BRIEF DESCRIPTION OF THE DRAWING

FIG. 1 is a schematic illustration of the process of the invention

In the following, the process according to the invention will be explained by way of example with reference to FIG. 1 of the drawing and the associated material stream table.

Legend for FIG. 1

| 18 | scrubber |
|---|---|
| 19 | gas separator |
| 20 | pump |
| 21 | cooler |
| 22 | condenser or blower |
| 23 | heater |
| 24 | fluidized-bed reactor with heater |
| 25 | cooler |
| 26 | separator |
| 27 | crystallizer |
| 28 | separator |
| 29 | condenser or blower |
| 30 | cooler |

Liquid urea, as starting material for the production of melamine, is fed into the gas separator (19) and is circulated as washing liquid for use in the scrubber (18) by means of the pump (20) via a cooler (21). In the scrubber (18), residues of isocyanic acid present in the process gas stream (15) are converted into urea by an exothermal chemical reaction. The reaction heat produced is discharged from the circulated urea by means of the cooler (21). From the urea circuit of the scrubber a urea stream (2) is branched off, mixed with an ammonia stream (3) and charged into the fluidized-bed reactor (24). From the process gas stream (4) treated in the scrubber (18) and the process gas stream (16) guided past the scrubber the process gas stream (5) is formed, which is supplied to the condenser or blower (22). The mixing ratio of the material streams (4) and (16) is adjusted such that the process gas stream (5) is supplied to the condenser or blower (22) with a temperature of 200° C. At this temperature, there is no risk of the formation of urea deposits or thermal overload of the conveying means. The process gas stream (16) can be cooled by means of the cooler (30) and/or by feeding a cool material stream (3') containing gaseous or liquid ammonia, so that its amount as compared to the material stream (4) can be increased without changing the temperature of the gas mixture.

Via the heater (23), the process gas (5) is delivered into the fluidized-bed reactor (24) as fluidizing gas. In an endothermal chemical process in the fluidized-bed reactor, in the presence of a catalyst, via the intermediate product isocyanic acid urea is converted into gaseous melamine and by-products, chiefly melem and melam. The fluidized-bed reactor is equipped with a heater which supplies the necessary reaction heat. The process gas loaded with the reaction products leaves the reactor as material stream (7), is cooled in the cooler (25) to such an extent that the by-products crystallize out, so that the same can be separated in the succeeding separator (26), together with catalyst particles entrained from the fluidized-bed reactor. The process gas thereafter still loaded with melamine is passed into the crystallizer (27), in which it is mixed with a process gas coming from the scrubber (18) and cooled. Melamine thereby is crystallized out, which in the succeeding separator (28) is separated from the process gas and after leaving the separator is present as process product material stream (13). From the separator (29), the process gas is guided as material stream (14) to the beginning of the process by means of the condenser or blower (29), in order to be treated as material stream (15) in the scrubber (18) and be guided past the scrubber as material stream (16). Due to this circulation of the process gas, process gas is present in excess, so that a part must be discharged from the process gas circuit as material stream (17).

Material Stream Table**):

| | Material stream no. | | | | | | | | | | | | | | | | |
|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 |
| Urea | x | x | | | | | | | | | | | | | | | |
| Ammonia | | | x | | | | | | | | | | | | | | |
| Process gas ($NH_3 + CO_2$) | | | | x | x | x | x | x | | x | x | x | | x | x | x | x |
| Melamine | | | | | | | x | x | | x | | x | x | | | | |
| By-product + catalyst residues | | | | | | | x | x | x | | | | | | | | |

-continued

Material Stream Table**):

| | | Material stream no. | | | | | | | | | | | | | | | | |
|---|---|---|---|---|---|---|---|---|---|---|---|---|---|---|---|---|---|
| | | 1 | 2 | 3 | 4 | 5 | 6 | 7 | 8 | 9 | 10 | 11 | 12 | 13 | 14 | 15 | 16 | 17 |
| Flow rate | t/h | 10 | 11 | 0.2 | 16 | 31.1 | 31.1 | 37 | 37 | 0.04 | 37 | 105 | 142 | 3.2 | 139 | 123.7 | 15.1 | 7.0 |
| Temp. | ° C. | 138 | 138 | 150 | 138 | 200 | 390 | 390 | 340 | 340 | 340 | 138 | 210 | 210 | 231 | 231 | 231 | 138 |
| State of matter | *) | li | li | g | g | g | g | g | g, s | s | g | g | g, s | s | g | g | g | g |

*) li = liquid  g = gaseous  s = solid
**) Exemplary procedure, without use of the cooler (30) and without feeding ammonia (3') into the partial stream (16)

The invention claimed is:

1. A process for the continuous production of melamine, wherein in a fluidized-bed reactor, in the presence of a catalyst, by supplying heat and by adding ammonia, the liquid urea used as starting material is converted into a process gas, chiefly consisting of melamine, ammonia, carbon dioxide, the intermediate product isocyanic acid and by-products, and wherein this process gas, after the by-products and the melamine have been separated therefrom, is passed into a scrubber in which it is washed with liquid urea and liberated from the isocyanic acid content, wherein the process gas, after leaving the scrubber, in part is used as fluidizing gas in the fluidized-bed reactor, in part is used as cooling gas in the crystallizer, and in part is discharged from the process gas circuit, wherein in flow direction before the scrubber a partial stream is branched off from the process gas stream, guided past the scrubber, and in flow direction before the fluidized-bed reactor introduced into the process gas stream serving for fluidization and treated in the scrubber.

2. The process according to claim 1, wherein an indirect heat exchanger is installed in the conduit of the partial stream, for cooling the same.

3. The process according to claim 1 wherein ammonia is fed into the conduit of the partial stream.

4. The process according to claim 1, wherein a static mixer is installed in conduit in flow direction before the conveying means.

* * * * *